United States Patent
Cognome Dotta

(10) Patent No.: US 7,766,166 B2
(45) Date of Patent: Aug. 3, 2010

(54) MULTIPLE PACKAGING OF WRAPPERS CONTAINING PRODUCTS FOR MEDICAL USE

(75) Inventor: Angelo Cognome Dotta, Bologna (IT)

(73) Assignee: Angelo Dotta, Bologna (IT)

( * ) Notice: Subject to any disclaimer, the term of this patent is extended or adjusted under 35 U.S.C. 154(b) by 388 days.

(21) Appl. No.: 11/630,797

(22) PCT Filed: Jun. 24, 2005

(86) PCT No.: PCT/IB2005/002040

§ 371 (c)(1),
(2), (4) Date: Dec. 3, 2007

(87) PCT Pub. No.: WO2006/003503

PCT Pub. Date: Jan. 12, 2006

(65) Prior Publication Data

US 2008/0190799 A1 Aug. 14, 2008

(30) Foreign Application Priority Data

Jun. 28, 2004 (IT) .......................... TO2004A0434

(51) Int. Cl.
*B65D 75/00* (2006.01)
(52) U.S. Cl. .......................... 206/438; 206/441; 229/84

(58) Field of Classification Search .................. 206/96, 206/102, 440–441, 438, 472–475, 495; 229/72, 229/84; 602/41–57
See application file for complete search history.

(56) References Cited

U.S. PATENT DOCUMENTS

| 3,899,077 | A | * | 8/1975 | Spiegelberg | ................ 206/441 |
| 4,194,624 | A | | 3/1980 | Spiegelberg | |
| 5,133,477 | A | | 7/1992 | Etheredge, III et al. | |
| 5,511,689 | A | | 4/1996 | Frank et al. | |
| 6,018,092 | A | | 1/2000 | Dunshee et al. | |
| 6,124,522 | A | * | 9/2000 | Schroeder | ..................... 602/57 |
| 6,225,522 | B1 | | 5/2001 | Schroeder | |
| 6,918,488 | B2 | * | 7/2005 | Renhed | ....................... 206/440 |
| 7,445,142 | B2 | * | 11/2008 | Salani et al. | ................... 229/72 |
| 7,521,586 | B2 | * | 4/2009 | Schroeder | ..................... 602/57 |

* cited by examiner

*Primary Examiner*—Bryon P Gehman
(74) *Attorney, Agent, or Firm*—Sughrue Mion, PLLC

(57) ABSTRACT

Multiple packaging of wrappers containing products for medical use include an envelope to which at least two bunches of the wrappers are fastened, the bunches being arranged so that the envelopes of each bunch turn out to be mutually joined along one side and free along the opposite side so as to appear spread apart. The bunches are fastened inside the envelope so to allow maximizing the multiple packaging capacity, without having to considerably increase the size.

20 Claims, 4 Drawing Sheets

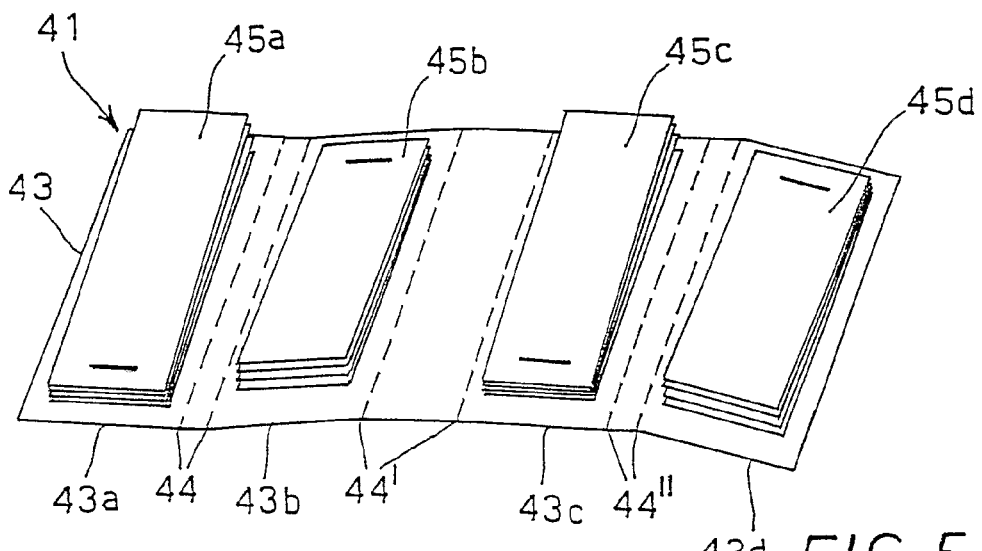
FIG. 5
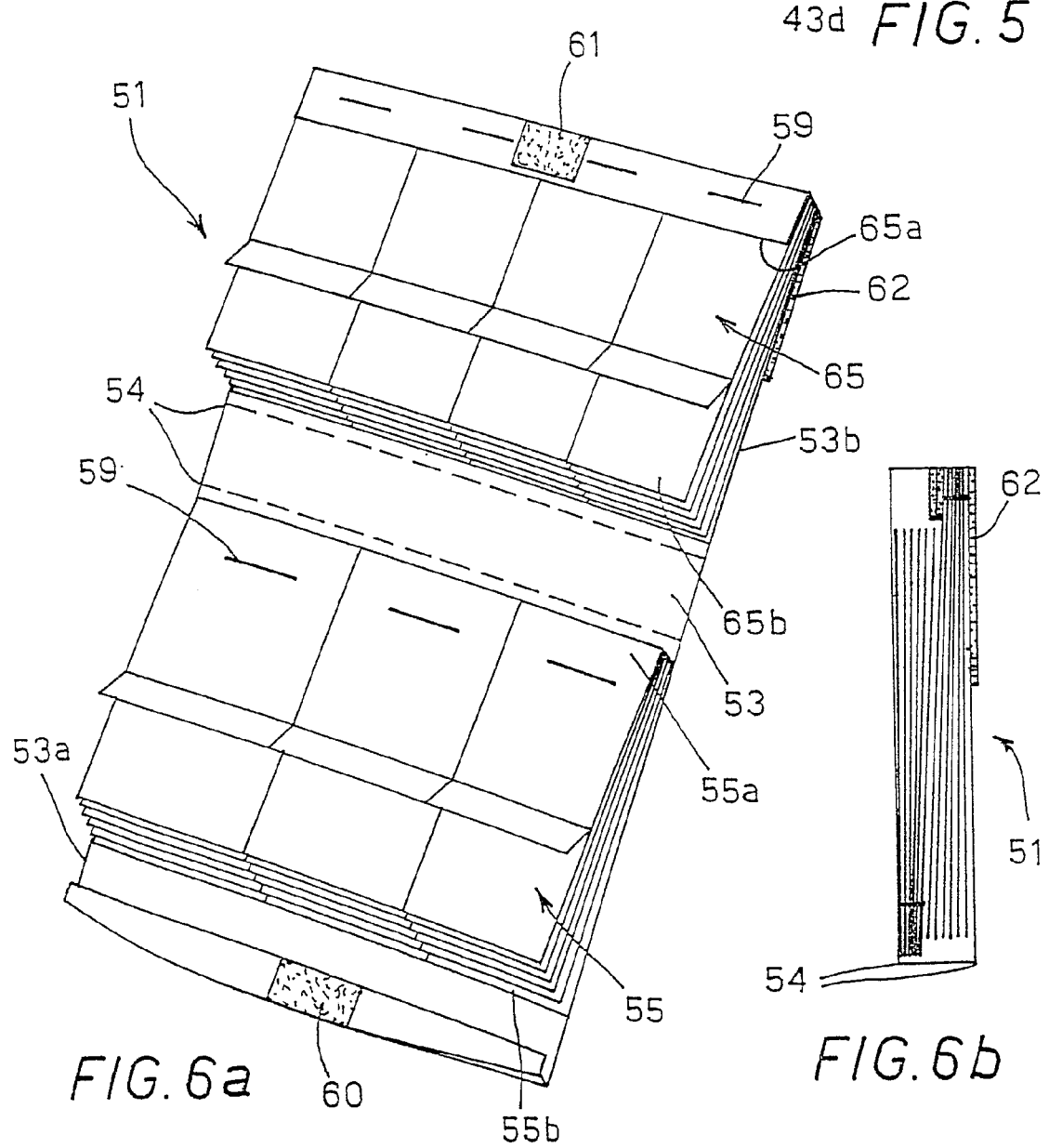
FIG. 6a
FIG. 6b

MULTIPLE PACKAGING OF WRAPPERS CONTAINING PRODUCTS FOR MEDICAL USE

The present invention refers to a multiple packaging of wrappers containing products for medical use. More precisely, the invention refers to a multiple packaging of wrappers containing products for medical use, such as adhesive bandages, plasters, disinfection or wound cure means.

As it is known, packagings already exist in which a plurality of wrappers containing adhesive bandages, instead of being loosely inserted inside a box, are fan-shaped assembled and fastened to a generally thin paperboard support, which contains them, in an arrangement recalling that of the ordinary matches packagings.

An example of packagings of adhesive bandages according to the know art above described is proposed in GB 904,632, that discloses a multiple packaging of adhesive bandages formed by an envelope inside which a series of overlain adhesive bandages is housed, to be extracted one at a time in case of need.

U.S. Pat. No. 4,194,624 discloses a closable envelope for a multiple packaging of adhesive bandages, wherein a plurality of wrappers is organized in a packaging, housed in its turn inside a closable envelope, which can be fixed to a support, for instance a wall, from which envelope said bandages are directly extractable one at a time in case of need.

U.S. Pat. Nos. 6,225,522, 6,124,522 and US2004/0004014 similarly disclose a packaging of adhesive bandages comprising an envelope consisting of a single paperboard sheet, folded so as to form a rear portion, onto which two side by side units of overlain wrappers are fixed, each of them containing an adhesive bandage, and an overturning free front portion, acting as a cover. The wrappers are fixed to the envelope with a staple or with a sticker one over another on the same side, while the opposite side is left free for extraction by the user. A drawback of the kind of packagings according to the known art is that the arrangement itself of the wrappers inside said packagings considerably limits the packaging content with respect to the actual size and to the capacity of the packaging itself: as a matter of fact, at the point where they are fixed to the envelope, the wrappers are mutually compressed, while on the opposite side, the free one, they fan out, with the consequence of occupying more room than that they will occupy if they were loosely housed without constraints inside the packaging.

Therefore, it is not taken advantage of all the useful room of the packaging, to the disadvantage of number of wrappers that the packaging can contain and of their assortment.

The object of the present invention is therefore to provide a multiple packaging of wrappers containing products for medical use such that, the size being equal, its actual capacity is utilize in a better way than the packagings available on the market.

This and other objects are achieved with the multiple packaging of wrappers containing products for medical use, as claimed in the attached claims.

Advantageously, according to the invention the content of the multiple packaging is nearly doubled, without having to considerably increase the size, thanks to the particular alternate arrangement of the bunches of wrappers inside the packaging. Moreover, the increased capacity of the multiple packaging of wrappers according to the invention allows to have at one's disposal a better assortment of products for medical use inside a single packaging. According to an embodiment of the invention, thanks to the same principle relevant to the particular arrangement of the wrappers inside the packaging, multiple packagings of wrappers containing products for medical use are provided, wherein, besides a high assortment of wrappers inside a single packaging having limited size, the wrappers are made promptly accessible by the user thanks to convenient ways of opening and closing of the packaging and to convenient closing and clamping means of the same to a fixed support.

The invention will be now described more in detail with reference to the enclosed figures, in which:

FIG. 1a schematically shows a perspective view of a multiple packaging of wrappers containing products for medical use according to the known art, in an open configuration;

FIG. 5 shows a fourth embodiment of the packaging according to the invention;

FIGS. 6a and 6b show a fifth embodiment of the packaging according to the invention;

Figure 1A:
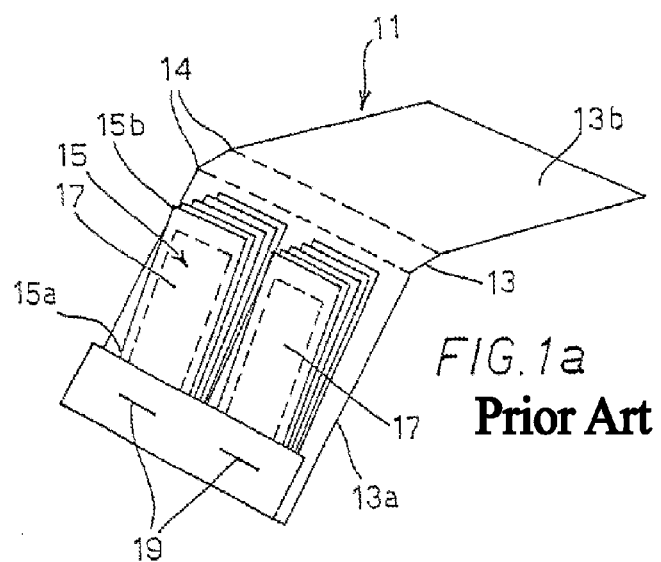
FIG. 1b is a schematic lateral view of the packaging of FIG. 1a, in a closed configuration.
Figure 1B:
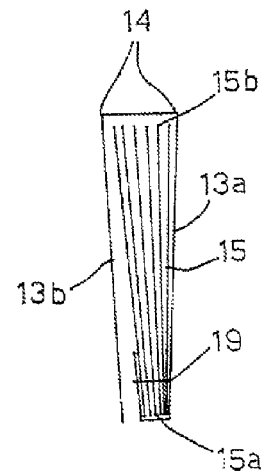

With reference to FIG. 1a, an example of multiple packaging 11 according to the known art, in an open configuration, is shown, comprising an envelope 13, consisting, in its turn, of a first portion 13a onto which a plurality of overlain wrappers 15 is fixed, and a second portion 13b foldable along the folding lines 14. Said wrappers 15, each containing, in the shown example, an adhesive bandage 17, are fixed to said first portion 13a of said envelope 13 by means of clasps or stitches 19 at level of a same constrained side 15a. The free side 15b of each of said wrappers 15 fans out at the opposite side. As shown in FIG. 1b, said multiple packaging 13 can be closed by folding and overturning the second portion 13b of said envelope 13 along said folding lines 14.

With reference to FIGS. from 2a to 6b, some embodiments of the multiple packaging of wrappers containing products for medical use according to the invention, in closable format, are shown.

Figure 2A:
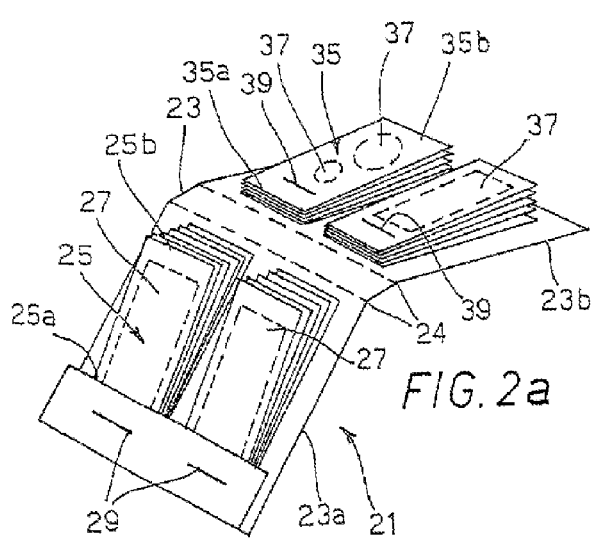
FIG. 2a is a schematic perspective view of the packaging according to a first embodiment of the invention, in an open configuration.

FIG. 2a shows a closable multiple packaging 21 of wrappers containing products for medical use, for instance adhesive bandages, according to the invention, in an open configuration, said packaging comprising an envelope 23 consisting of a first portion 23a and of a second portion 23b, defined by one or more folding lines 24. A first plurality of wrappers 25 is fastened, in two side by side series, onto said first portion 23a by means of clasps or stitches 29. A second plurality of wrappers 35 is fastened, in two side by side series, onto said second portion 23b by means of clasps or stitches 39. In FIG. 2a, by way of example, said pluralities of wrappers 25,35 are shown in number of two series or bunches of overlain wrappers that folding open on each portion 23a,23b of said envelope 23, said bunches in their turn being formed by 5 wrappers each.

Said packaging 21 can be closed by folding the second portion 23b of said envelope 23 along the folding lines 24 toward said first portion 23a.

Figure 2B:
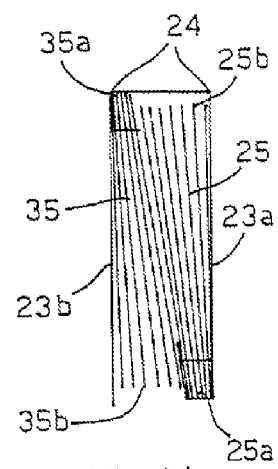
FIG. 2b is a schematic lateral view of the packaging of FIG. 2a, in a closed configuration.

In particular, as it appears evident from FIG. 2b, the arrangement of the wrappers 25,35 is such that, when the packaging is closed, said constrained side 25a of the wrappers 25 on the first portion 23a and said free side 35b of the wrappers 35 on said second portion 23b turn to be faced and, correspondingly, said free side 25b of the wrappers 25 and said constrained side 35a of the wrappers 35 fastened to said second portion turn to be faced too. In other words, the joined side of one of said bunches and the free side of a second of said bunches are turned in the same direction, said bunches of wrappers being mutually faced with reversed direction.

Thanks to such arrangement of the wrappers, the capacity of the envelope is maximized, up to double the number of wrappers with respect to the packaging according to the known art of FIG. 1a, without considerably modifying the packaging size. All this with considerable advantage for the user, since he can have at his disposal a greater assortment of bandages of different sizes and shapes inside a single packaging.

Figure 3:
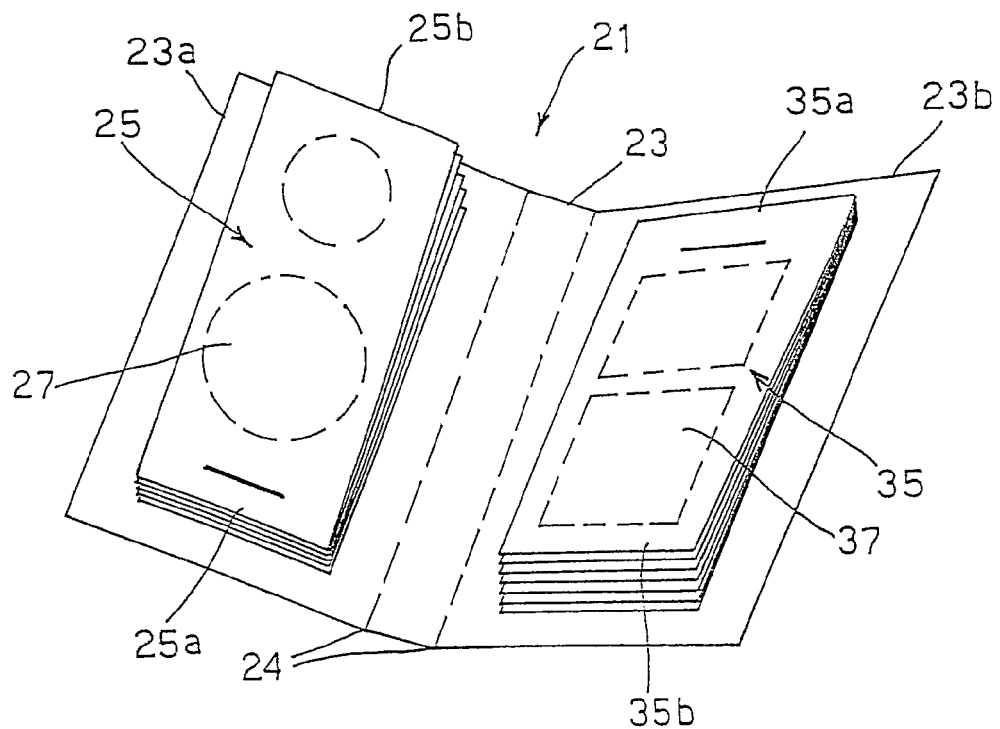
FIG. 3 shows a second embodiment of the packaging according to the invention.

Always according to the same principle described above, FIG. 3 shows a variant of the multiple packaging 21 of FIG. 2a, in an open configuration, characterized by a "book" closing type.

Referring now to FIGS. from 4a to 5, two further embodiments of the invention are shown.

Figure 4A:
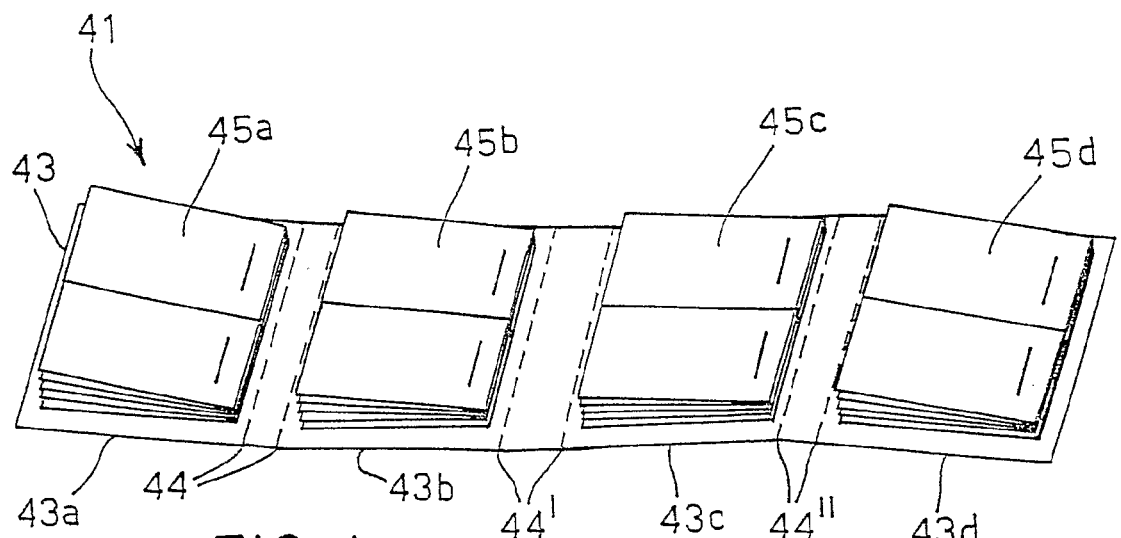
FIGS. 4a and 4b show a third embodiment of the packaging according to the invention.
Figure 4B:
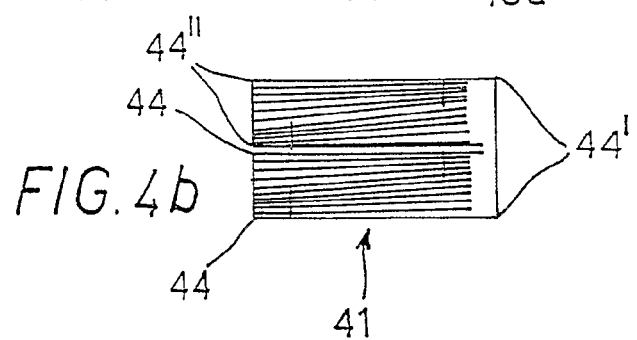

FIGS. 4a and 5 show a closable multiple packaging 41 of wrappers containing products for medical use, for instance adhesive bandages, in an open configuration, wherein the envelope 43 consists of more portions 43a,43b,43c,43d (in FIGS. 4a and 5, for instance, the shown envelope 43 consists of 4 portions), each provided, respectively, of a plurality of wrappers 45a,45b,45c,45d. Each of said pluralities of wrappers 45a,45b,45c,45d, as for instance shown in FIG. 4a, can be organized in two or more separate bunches or, as shown in FIG. 5, in a single bunch, and it is fastened to said envelope 43 according to a direction such that, being the packaging closed, said pluralities of wrappers 45a,45b,45c,45d overlie one over another so that the constrained side of one corresponds to the free side of the other. For instance, said multiple packaging 41 can be closed by folding firstly the outer portions 43a, 43d respectively along the folding lines 44, 44" and, then, by folding said envelope 43 along the inner folding lines 44', so as to obtain the "double book" closed packaging shown in FIG. 4b. More in general, according to this embodiment the multiple packaging is such that the envelope is divided into four portions, the first one of which is clockwise/counterclockwise foldable by facing its own bunch of wrappers to the bunch of wrappers of the second portion, the fourth one of which is counterclockwise/clockwise foldable by facing its own bunch of wrappers to that of the third portion, both the resulting portions being correspondingly foldable thus creating a single compact packaging thanks to that inside the envelope at least two parallel folding lines are provided, in median position, conveniently mutually spaced.

It is evident that, thanks to the principle with which said pluralities of wrappers 45a,45b,45c,45d are arranged and thanks to the presence and of the position of the folding lines 44,44',44", it is possible to provide packagings the closing of which occurs according to other ways, for instance by sequentially folding said portions 43a,43b,43c,43d one over another.

With reference to FIGS. 6a and 6b, a further embodiment of the invention is shown. FIG. 6a shows an open multiple packaging 51, wherein the envelope 53 consists of a first portion 53a and of a second portion 53b defined by two folding lines 54. Onto both said portions 53a,53b are respectively fastened, by means of clasps or stitches 59, pluralities of wrappers 55,65 containing, in the shown example, adhesive bandages. The free sides 55b,65b of said wrappers 55,65 appear to be all directed in the same direction, i.e. downward in the figure. Said multiple packaging 51, moreover, has means 62 fitted to assure the clamping of said packaging 51 to a fixed support, for instance a wall. Said means 62 can for instance consist in a biadhesive tape strip.

When said multiple packaging 51 is fixed to the wall and it is open, the user can easily access to the wrappers 55,65 containing the adhesive bandages and, as much easily, he can then close said packaging 51 by folding and overturning said portion 53a of said envelope 53 along the folding lines 54 until making said pluralities of wrappers 55,65 to mutually face, as shown in FIG. 6b. To this purpose, said packaging 51 is advantageously provided with closing means 60,61, for instance consisting in Velcro™ or similar material, which conveniently maintain the packaging 51 closed until a new employ.

Advantageously, the multiple packaging 51 according to the invention, besides a considerable assortment of adhesive bandages and an easier opening/closing, thanks to the presence of said support means 62 and closing means 60,61 it can also act as supplier/dispenser of adhesive bandages. The employ of such a multiple packaging appears to be particularly suitable for that cases in which an adequate and constant assortment of bandages always available and of quick use is required in a certain place (school, workplace, etc.).

Always according to the same principle of alternate overlying the bunches of wrappers, hereinafter are proposed two further embodiments of the multiple packaging according to the invention, wherein the envelope permanently takes up the shape of a box.

Figure 7A:
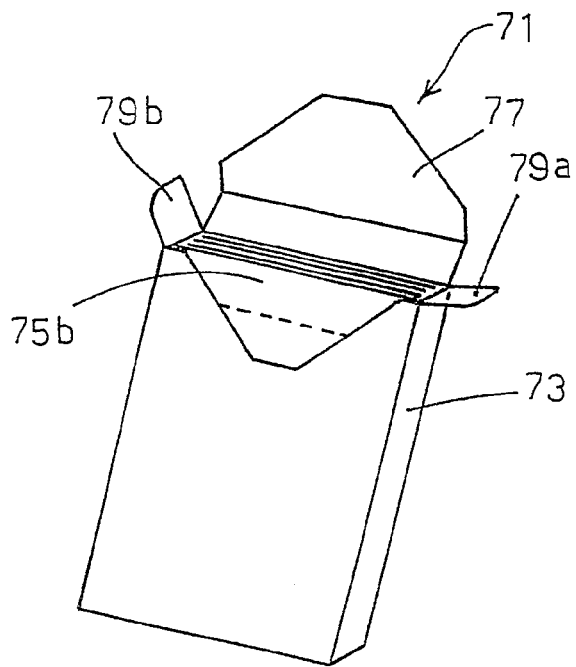
FIGS. 7a and 7b show a sixth embodiment of the packaging according to the invention.
Figure 7B:
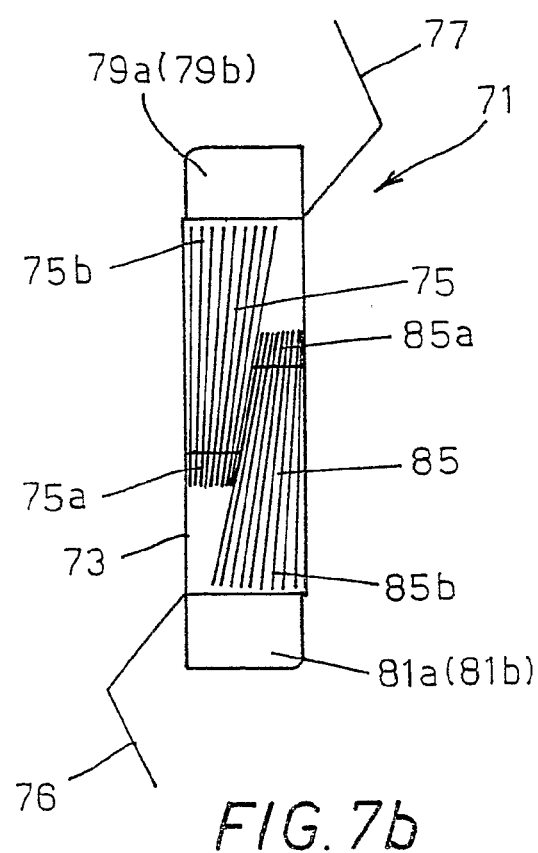

In particular, FIGS. 7a and 7b show a sixth embodiment of the invention according to which a multiple packaging 71 has an envelope 73 consisting of a box having two closable openings. Inside it, by way of example, two pluralities of wrappers 75,85 fastened to said envelope 73 are shown. Onto each of said two sides of said envelope 73 corresponding to the free sides 75b,85b of said wrappers 75,85, said envelope 73 has a central winglet 76,77 and a couple of lateral winglets 79a, 79b; 81a, 81b. In order to close said envelope 73, it will be sufficient to fold up said lateral winglets 79a, 79b; 81a, 81b and said central winglet 76,77 toward inside said envelope 73; on the contrary, it will be sufficient to fold up said winglets toward outside to open said envelope 73 and to make said free sides 75b,85b of said wrappers 75,85 accessible by the user.

Figure 8A:
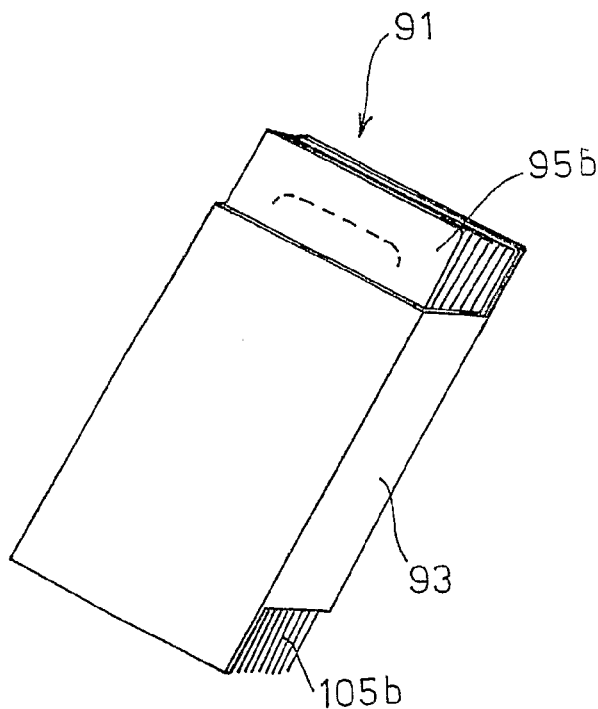
FIGS. 8a and 8b show a seventh embodiment of the packaging according to the invention.
Figure 8B:
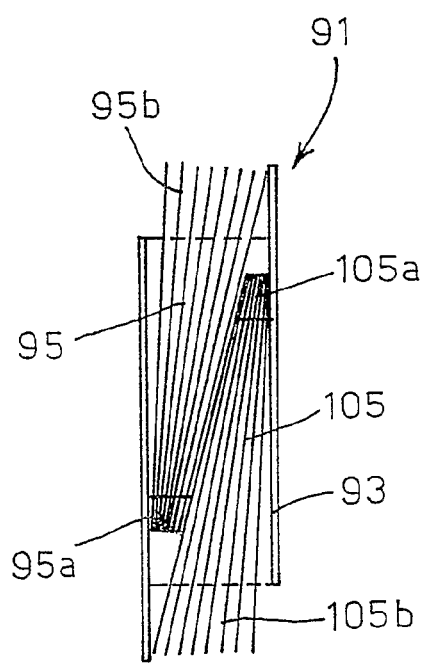

FIGS. 8a and 8b show a seventh embodiment of the multiple packaging 91 according to the invention, wherein said envelope 93 has the shape of a box having two permanent openings in correspondence with said free sides 95b,105b of said wrappers 95,105, said free sides conveniently projecting with respect to said envelope 93 in order to facilitate the access to said wrappers 95,105 by the user.

Said container 93 is preferably rigid. As it will be noticed, in the embodiments shown in FIGS. 7a-8b, the bunches of wrappers are conveniently staggered, so as to make the free side of the wrappers easily accessible.

In all of its embodiments, the multiple packaging of wrappers according to the invention can be arranged with wrappers containing assorted heterogeneous products. Moreover, medical products into conventional wrappers can be employed, to be slipped out simply by pulling the free end. In this case, the wrappers will preferably have, downstream the fastening point to the envelope, an indentation or another trick that allows the tear thereof without jeopardizing the integrity of the wrapper itself. The multiple packaging according to the invention can be arranged also by employing fast opening adhesive bandages of the type described for instance in U.S. Pat. Nos. 4,235,337, 4,418,822 and 6,719,137 in the name of Dotta. In this last case, the traction of the wrapper from its free side will directly cause its opening and the adhesive bandage will be already ready to be employed by the user. The employ of fast opening adhesive bandages is particularly appropriate in the case of the packaging shown in FIGS. 6a and 6b.

Advantageously, for manufacturing the multiple packaging according to the invention materials of different kinds can be employed, easily available, being easily manufactured and at low costs, such as, for instance, paper, paperboard, plastics, metal, etc.

Needless to say that, besides the adhesive bandages, the employ of the multiple packaging according to the present invention can be extended to all that range of products that need to be preserved in a closed wrapper until the moment of being used, but above all that need to be promptly and easily available (serviettes, medicated or disinfectant tampons, plasters, disposable products in general, etc.).

Though the invention has been described and illustrated with reference to the above-mentioned embodiments, it will be possible, by following the ordinary knowledge of the skilled in the art, to achieve further variants that will not differ from the protective scope claimed in the enclosed claims.

The invention claimed is:

1. A multiple packaging of rectangular shaped wrappers containing products for medical use comprising an envelope to which at least two bunches of said wrappers mutually overlain are fastened, said bunches being arranged so that the wrappers of each bunch turn out to be mutually joined along a first side with free second sides, opposite to the first side, spread apart, wherein said bunches are fastened to said envelope so that, when said packaging is closed, the joined first side of each of said wrappers of a first one of said bunches and the free second side of each of said wrappers of a second one of said bunches are arranged directed in a same direction, said bunches of wrappers being arranged in opposite directions with respect to each other.

2. A packaging according to claim 1, wherein said envelope shows folding lines in order to define two or more portions of said envelope, onto each of which a corresponding bunch of wrappers is fastened, said multiple packaging being closable by folding up said portions of said envelope correspondingly along said folding lines.

3. A packaging according to claim 2, wherein said bunches of wrappers are oriented in one of two different directions, having said joined first sides all parallel or, alternatively, all perpendicular with respect to said folding lines delimiting the two or more portions of said envelope.

4. A packaging according to claim 3, wherein said envelope is divided into four portions, including a first portion, a second portion, a third portion and a fourth portion, wherein the first portion is clockwise foldable by facing the bunch of wrappers of the first portion to the bunch of wrappers of the second portion thereby forming a corresponding first folded portion, the fourth portion is counterclockwise foldable by facing the bunch of wrappers of the fourth portion to that of the third portion thereby forming a corresponding second folded portion, both said first and second folded portions being correspondingly foldable thus creating a single compact packaging, inside the envelope at least two parallel folding lines being provided, in median position, conveniently mutually spaced.

5. A packaging according to claim 3, wherein said envelope is divided into four portions, a first portion is counterclockwise foldable by facing the bunch of wrappers of the first portion to the bunch of wrappers of a second portion thereby forming a corresponding first folded portion, a fourth portion is clockwise foldable by facing the bunch of wrappers of the fourth portion to that of a third portion thereby forming a corresponding second folded portion, both said first and second folded portions being correspondingly foldable thus creating a single compact packaging, inside the envelope at least two parallel folding lines being provided, in median position, conveniently mutually spaced.

6. A packaging according to claim 2, wherein onto each of said portions of said envelope at least two side by side bunches of said wrappers are fastened, able to contain assorted products.

7. A packaging according to claim 1, wherein said envelope comprises two permanent opposed openings through which the free second side of each of said wrappers is accessible for their extraction.

8. A packaging according to claim 1, wherein said envelope is substantially rigid.

9. A packaging according to claim 1, wherein said envelope is formed by a box having two openings, each of them being closable by folding up, toward inside said envelope, a central winglet and a couple of lateral winglets.

10. A packaging according to claim 1, wherein said envelope is formed by a box having two opposed permanent openings.

11. A packaging according to claim 1, wherein on said envelope a closing means or a clamping means to a fixed support is provided.

12. A packaging according to claim 11, wherein said closing means is a tear opening type.

13. A packaging according to claim 12, wherein the closing means is a micro hook loop fastener.

14. A packaging according to claim 11, wherein said clamping means consists of biadhesive tape.

15. A packaging according to claim 11, wherein, when said multiple packaging is fixed to a support in an open position, said wrappers have their free second sides turned downward.

16. A packaging according to claim 1, wherein said products for medical use comprise adhesive bandages of a fast opening type.

17. A packaging according to claim 1, wherein said products for medical use comprise at least one of adhesive bandages, plasters, serviettes, medicated tampons, disinfectant tampons and other disposable products.

18. A packaging according to claim 1, wherein said packaging is arranged with wrappers containing heterogeneous assorted products.

19. A packaging according to claim 1, wherein said packaging is arranged with wrappers containing adhesive bandages and disinfectant tampons.

20. A packaging according to claim 1, wherein, when said packaging is closed, the first one of said bunches overlaps with the second one of said bunches, and the first one and the second one of said bunches of wrappers are arranged in opposite directions with respect to each other, such that the joined first sides of the first one of said bunches overlie the free second sides of the second one of said bunches and the joined first sides of the second one of said bunches overlie the free second sides of the first one of said bunches.

* * * * *